United States Patent [19]

Brown et al.

[11] Patent Number: 4,959,353
[45] Date of Patent: Sep. 25, 1990

[54] PROMOTION OF CORNEAL STROMA WOUND HEALING WITH HUMAN EPIDERMAL GROWTH FACTOR PREPARED FROM RECOMBINANT DNA

[75] Inventors: Gregory L. Brown, Atlanta, Ga.; Richard Eiferman; Gregory L. Schultz, both of Louisville, Ky.; Valenzuela, Pablo D. T., San Francisco, Calif.

[73] Assignees: University of Louisville Foundation, Louisville, Ky.; Chiron Corporation, Emeryville, Calif.

[21] Appl. No.: 41,695

[22] Filed: Apr. 23, 1987

Related U.S. Application Data

[63] Continuation-in-part of Ser. No. 663,092, Oct. 19, 1984, abandoned.

[51] Int. Cl.$^5$ .................... A61K 37/36; C12P 21/02
[52] U.S. Cl. ........................ 514/12; 514/912; 435/69.1
[58] Field of Search ............ 435/68, 172.3, 317; 935/6, 8, 37, 48, 49; 424/95; 514/12, 912

[56] References Cited

U.S. PATENT DOCUMENTS 4,526,938  7/1985  Churchill et al. ............... 525/415
4,588,684  5/1986  Brake ............................... 435/68
4,708,861 11/1987  Popescu et al. .................. 424/1.1

FOREIGN PATENT DOCUMENTS 0046039  2/1982  European Pat. Off. ......... 435/172.3

OTHER PUBLICATIONS

Albrecht v. *Graefes Arch klin exp Ophthal* (1979), 210:159–65.
Carpenter, *Handbook of Exp. Pharmacology*, vol. 57:90–132 (1981).
Urdea et al., *PNAS*, 80:7461–7465 (Dec. 1983).
Rothstein et al., *Meth. Enzy.* 68:98–109 (1979).
Bennetzen et al., *J. Biol Chem.* 257(6): 3026–3031 (Mar. 25, 1982).
Fabricant et al., *Arch. Opthalmol.*, 100:994–995 (1982).
Kurjan et al., *Cell,* 90:933–943 (Oct. 1982).
Greaves, *Clin. Exp. Dermatol.*, 5:101–103 (1980).

*Primary Examiner*—Elizabeth C. Weimar
*Assistant Examiner*—Marian C. Knode
*Attorney, Agent, or Firm*—Irell & Manella

[57] ABSTRACT

A method for treating corneal stromal wounds to promote regeneration of the affected tissue is provided. This method employs recombinant human epidermal growth factor.

21 Claims, No Drawings

PROMOTION OF CORNEAL STROMA WOUND HEALING WITH HUMAN EPIDERMAL GROWTH FACTOR PREPARED FROM RECOMBINANT DNA

CROSS-REFERENCE TO RELATED APPLICATION

This application is a continuation-in-part of copending application U.S. Serial No. 663,092, filed 19 Oct. 1984, now abandoned.

BACKGROUND OF THE INVENTION

1. Field of the Invention

Wounds resulting from cuts, abrasions, burns, skin ulcers, skin grafts, and the like can affect large areas of the skin and require lengthy periods to heal. Long healing times are a particular problem with wounds on sensitive areas, such as corneal wounds, which are difficult to treat over prolonged periods. For these reasons, there has been a long-felt need for a pharmacological agent which will promote rapid healing of skin and corneal wounds.

Heretofore, a number of research groups have investigated the use of epidermal growth factor obtained from mouse salivary glands (mEGF) to promote the regeneration of epidermal wounds. Thus far, the treatment of relatively large wounds resulting from abrasions, burns, and the like with mEGF has proved to be of only marginal value in promoting wound healing. Although the use of mEGF in promoting healing of corneal epithelial wounds has been more promising, such treatment has not been shown to be effective in accelerating the rate of healing of corneal stromal wounds.

It would thus be desirable to provide a method and agent for treating epithelial, stromal and corneal wounds which will promote the rapid healing of these wounds. In particular, it would be desirable to provide such an agent in large quantities and in formulations which are suitable for treatment of the affected area.

2. Description of the Prior Art

A comparison of human and mouse epidermal growth factor (EGF) and a discussion of their activities in vivo and in vitro are presented in Hollenberg, "Epidermal Growth Factor-Urogastrone, a Polypeptide Acquiring Hormonal Status", Academic Press, Inc., New York (1979), pp. 69–110. See also Carpenter, "Epidermal Growth Factor" in Handbook of Experimental Pharmacology, Vol. 57, Baserga, ed., Springer Verlag, Berlin (1981), pp. 90–132; and Carpenter (1979) *Ann. Rev. Biochem.* 48: 193–216.

Various studies have examined the use of mEGF in treating epidermal wounds. Greaves (1980) *Clin. Exp. Dermatol.* 5: 101–103, applied mEGF on blister wounds on human subjects. The mEGF in saline solution was applied once daily until the wounds healed. No acceleration in the growth of the epidermal layer was observed. Topical application of mEGF to open wounds in mice has been found to promote healing in various degrees. See, e.g., Niall et al. (1982) *J. Surg. Res.* 33: 164–169; Thornton et al. (1981) *Burns* 8: 156–160.

The use of mEGF to promote the healing of corneal epithelial wounds has been described. See, e.g., Daniele et al. (1979) *Graefes Archives Opththalmologie* 210: 159–165; Ho et al. (1974) *Invest. Ophthalmol.* 13: 804–809; Elliott (1980) *Trans. Amer. Ophthalmol. Soc.* 30: 629–656; and Gospodarowicz et al. (1977) *Exp. Eye Res.* 25: 75–89.

SUMMARY OF THE INVENTION

Methods and compositions for treating epithelial and stromal wounds to promote their rapid healing are provided. The method utilizes a treatment composition including a purified polypeptide having mitogenic activity capable of promoting the growth of both the epidermal and dermal layers of the skin as well as the epithelial and stromal layers of the cornea and other organs. Healing occurs, in part, as a result of the migration and multiplication of epithelial and stromal cells into the wound. The polypeptide is produced by recombinant DNA techniques, typically utilizing a synthetic gene having a nucleotide sequence based on the known amino acid sequence of human epidermal growth factor (hEGF). The compositions are applied topically to the affected area and include suitable carriers or bases. For general treatment of areas other than the cornea, the carrier will usually be an ointment or a cream, typically including an antibacterial agent. For corneal treatment, the carrier will be a suitable liquid or ointment.

DESCRIPTION OF THE SPECIFIC EMBODIMENTS

The present invention provides a method for treating cutaneous and corneal wounds to accelerate healing of the wounds in humans and other mammals. The method will also find use in treating other epithelial and stromal disruptions, such as chronic ulcers, burns, surgical wounds, and injuries to the hollow, epithelial lined organs, such as the esophagus, stomach, large and small bowels, mouth, and urinary tract. The method relies on the topical application of a treatment composition including a polypeptide having an amino acid sequence and mitogenic activity similar to that of hEGF. The polypeptide is produced in a microorganism from a gene encoding the amino acid sequence for hEGF. In the exemplary embodiment, the gene is a synthetic gene composed of codons preferentially recognized by yeast, and the microorganism host is yeast. By suitably purifying the resulting polypeptide product, and applying the polypeptide to the affected area in a physiologically acceptable carrier medium, it has been found that the rate of the healing process is substantially increased.

hEGF is a mitogenic polypeptide found in urine which is capable of stimulating the proliferation of keratinocytes and other mammalian epidermal cells in culture. The polypeptide exists as a 53 amino acid form ($\beta$-hEGF) and a 52 amino acid form ($\gamma$-hEGF), which forms are identical except that $\gamma$-hEGF lacks the C-terminal arginine residue found on $\beta$-hEGF. The amino acid sequences for both forms are reported in Hollenberg (1979), supra.

As used hereinafter and in the claims, human epidermal growth factor, or hEGF, will refer to a polypeptide product which is produced in a microorganism and which displays biological activity, e.g., mitogenic activity, similar to natural human epidermal growth factor protein as measured in recognized bioassays. The polypeptide product will have an amino acid sequence which is the same or substantially the same as the natural protein, usually differing by no more than five amino acids, more usually differing by three or fewer amino acids. For the most part, the hEGF amino acid sequence will differ, if at al, by substitutions among the nonpolar amino acids, e.g., aliphatic and aromatic amino acids. The deviations from the natural amino acid sequence will not adversely affect the mitogenic activity of the polypeptide product and its ability to promote epithelial healing. Prior to incorporation in a treatment composition, the hEGF polypeptide will be suitably purified (as described below) to remove other proteins and substances recovered from the microorganism host. Purification is essential to assure that undesirable activity resulting from other substances is no present in the treatment composition.

The hEGF polypeptide is obtained by expression of an hEGF gene in a suitable microorganism host, preferably a yeast host which can provide for secretion of the polypeptide as described below. The hEGF gene may be chromosomal DNA, cDNA, synthetic DNA, or a combination thereof, e.g., synthetic DNA may be combined with the cDNA to complete the hEGF gene. Conveniently, the present invention will utilize a synthetic DNA sequence encoding for the amino acid sequence of either $\beta$-hEGF or $\gamma$-hEGF. The hEGF gene will be incorporated in an extrachromosomal element including a replication system recognized by a desired host, typically yeast, and transcriptional and translational regulatory control sequences controlling the expression of the hEGF gene. The extrachromosomal element may include a number of other features, such as selectable markers, which facilitate manipulation of the element. The construction of a number of suitable extrachromosomal elements capable of producing hEGF polypeptides is described in copending application Serial No. 522,909, filed on 12 Aug. 1983, now abandoned, assigned to the assignee of the present invention, the relevant portions of which are incorporated herein by reference. Desirably, the extrachromosomal elements of the present invention will include a secretory leader and processing signal sequence in proper reading frame with the hEGF gene in order to provide host translational modification and secretion of the gene product. Secretion facilitates recovery of the polypeptide, allowing isolation from the culture medium without having to lyse the host. Moreover, secretion of the hEGF polypeptide avoids contamination of the hEGF with intracellular proteins and other substances which would be released by lysing the microorganism host.

Secretory leader and processing signal sequences suitable for the preferred yeast host will normally be derived from naturally occurring DNA sequences in yeast which provide for secretion of a polypeptide. Such polypeptides which are naturally secreted by yeast include $\alpha$-factor, a-factor, acid phosphatase, and the like. If desired, the naturally occurring sequence may be modified, for example, by reducing the number of lys-arg pairs which define the processing site (while retaining at least one pair), or by reducing the length of the mRNA leader (while retaining sufficient length to provide for secretion), or by introducing point mutations, deletions, or other modifications which facilitate manipulation, e.g., restriction recognition sites. Conveniently, the secretory leader and processing signal sequence may be joined to the hEGF structural gene by providing appropriate cohesive ends on the synthetic structural gene, by means of adaptor molecules, or a combination of both.

After the hEGF polypeptide has been recovered from the microorganism culture, it is necessary to purify the polypeptide to remove foreign proteins and other substances which might have an adverse effect on the compositions of the present invention. As stated above, purification is simplified and enhanced by providing for secretion of the hEGF polypeptide into the culture medium. Purification may then be accomplished as follows.

The yeast culture is centrifuged, and the supernatant medium is concentrated by pressure filtration and ultrafiltration. This concentrated solution, containing the secreted hEGF, is then submitted to ion exchange chromatography and the fractions containing hEGF activity are further purified by high performance liquid chromatography (HPLC). The hEGF peak obtained after HPLC will typically be greater than 95% pure.

The compositions of the present invention will be useful for testing a wide variety of wounds, including substantially all cutaneous wounds, as well as injuries to the cornea and epithelial lined hollow organs. Wounds suitable for treatment result from trauma such as burns, abrasions, cuts, and the like, as well as from surgical procedures such as surgical incisions and skin grafting. Other conditions suitable for treatment with the present invention include chronic conditions, such as venous stasis ulcers, diabetic ulcers, and other non-healing (trophic) conditions. The compositions while find particular use in treating corneal and scleral wounds, including wounds which affect the epithelial layer, stromal layer, and endothelial layer. Treatment according to the present invention will promote cell division of the endothelial layer of the cornea which was previously thought incapable of growth and regeneration.

The polypeptides will be incorporated in physiologically acceptable carriers for application to the affected area. The nature of the carriers may vary widely and will depend on the intended area of application. For application to the skin, a cream or an ointment base is usually preferred; suitable bases include lanolin, Silvadene ® (Marion) (particularly for the treatment of burns), Aquaphor ® (Duke Laboratories, South Norwalk, CN), and the like. If desired, it will be possible to incorporate the hEGF-carrier compositions in bandages and other wound dressings to provide for continuous exposure of the wound to the hEGF. Aerosol applicators may also find use.

For corneal treatment, the carrier will be suitable for application to the eyes. Suitable carriers include ointments, saline solutions, isotonic saline solutions, such as Sorbi-care ™ (Allergan Pharmaceuticals), Neodecadron ® (Merck, Sharp & Dohme), and the like. A suitable ointment base is sold under the tradename Lacrilube ®. The ocular carriers will normally include preservatives, such as edetate disodium, unless they are formulated immediately prior to application.

Often, it may be desirable to incorporate (e.g., encapsulate or disperse) the hEGF in carriers or vehicles such as liposomes, nonresorbable semipermeable polymers such as ethylene-vinyl acetate copolymers and Hytrel ® copolymers, swellable polymers such as hydrogels, or resorbable polymers such as collagen and certain polyacids such as those used to make resorbable sutures to provide for sustained release of the hEGF to the wound site over an extended time period, typically from 24 to 48 hours or longer, for instance, up to about one week. Such incorporation may be particularly desirable when the hEGF is incorporated into a wound dressing as described above. The mechanism of hEGF release from the formulation may be diffusion, osmosis, leaching, dissolution, erosion, or combinations thereof. In diffusional sustained release formulations the hEGF dissolves in and diffuses through the carrier or vehicle on which it is encapsulated/dispersed. In leaching or dissolution formulations, the hEGF is leached from the carrier by body fluids. The concentration of polypeptide in the treatment composition is not critical, usually; the polypeptide will be present at from at least 1 μg/ml, usually between 10 μg/ml and 10 mg/ml. The compositions may be applied topically to the affected area, typically as eye drops to the eye or as creams or lotions to the skin or implanted at the wound site. In the case of the eyes, frequent treatment is desirable, usually being applied at intervals of 4 hours or less. For cutaneous or stromal wounds it is desirable to continually maintain the treatment composition at the affected area or wound site during the healing period. This may be achieved via a multiplicity of intermittant applications of the treatment composition, e.g., from 2 to 4 times a day, or more frequently or by administering the hEGF via a sustained release dosage form such as those described above. In this regard, the term "continually" denotes true continuous administration such as is achieved by such sustained release dosage forms or that achieved by such repeated applications that provide a pharmacokinetic pattern that mimics that achieved by true continuous administration.

Optionally, the treatment compositions of the present invention may be combined with effective amounts of anesthetics, antibiotics, antiseptics, and other drugs, typically present at from about 0.001% to 2% by weight.

The following experimental results are offered by way of examples, not by way of limitation.

EXAMPLE 1

Materials and Methods

1. Preparation of hEGF Polypeptide

The hEGF polypeptide utilized in the following experiments was obtained by expression of plasmid pYα-EGF-23 in yeast strain AB103. Plasmid pYαEGF-23 was prepared as described in Brake et al. (1984) *Proc. Natl. Acad. Sci. U.S.A.* 81: 4642–4646. Plasmid pYα-EGF-23 contains a synthetic sequence for mature epidermal growth factor (hEGF) based on the amino acid sequence of EGF reported by Gregory and Preston (1977) *Int. J. Peptide Protein Res.* 9: 107–118. The hEGF gene is joined in its 5′ end to sequences encoding the promoter and leader region of the yeast mating pheromone α-factor, and in its 3′-end to the terminator sequences of the α-factor gene. This expression cassette for hEGF is cloned into a yeast shuttle vector, pCl/1, which contains yeast and bacterial origins of replication and genetic markers (amp$^R$ for bacteria, leu2 for yeast). Yeast cells transformed with plasmid pYαEGF-23 efficiently produce and secrete authentic biologically active hEGF into the medium (Brake et al., supra).

2. Purification of hEGF

The hEGF from the yeast cultures was purified by pressure filtration and ultrafiltration, followed by batch adsorption and elution from carboxylic acid ion-exchange resin (BioRex-70), in 0.1M acetic acid; and high performance liquid chromatography (HPLC). Supernatant broth (180 liters) from the yeast fermentation was submitted to pressure filtration through a cellulose membrane using several Spira/Por unit cartridges of up to 5 sq. ft. (Ultra/Por, MW cutoff 1K; Type "C" on Pellon). The final sample of 1 to 2 liters of filtered supernatant containing hEGF was further concentrated by ultrafiltration through an Amicon membrane (YM2, MW cutoff 2K) to yield 200–300 ml.

The column of 1700 ml of packed P-10 resin (Bio-Rad) was equilibrated with 2500 ml of 0.1M acetic acid. The 200 to 300 ml of concentrated hEGF-containing filtrate were passed through the column at 4° C. at a rate of 0.16 liter per hour. hEGF was recovered in the included volume of the column. The fractions containing hEGF were pooled (400 ml), and the pool was concentrated using an Amicon ultrafiltration membrane, as previously described (YM2, MW cutoff 2K). About 20 to 30 ml of solution, containing about 16 mg/ml of hEGF, was obtained. This solution was then filtered through a 0.45 μm Acrodisk.

The material obtained from the previous step was injected into a C4 reverse-phase HPLC column and eluted with a gradient of 5% to 80% acetonitrile in 0.05% trifluoroacetic acid, over approximately 55 minutes. The fractions containing the main hEGF peak were evaporated and freeze-dried. The material was stored as a dry powder.

3. Corneal Epithelial Wounds

The epithelial cells were removed completely from the corneas of anesthetized monkeys by n-octanol and scraping with a Bard-Parker #15 scalpel blade as confirmed by fluorescein staining. Monkeys received two drops three times a day of Neodecardron ® alone (control eyes) or containing hEGF (0.1 mg/ml). Each day eyes were stained with fluorescein and photographed. The extent of epithelial regeneration was measured quantitatively by planimetry of enlarged photographs using a Hewlett-Packard distizing table model (9874A). Each wound area was measured three times and the mean value was determined. The extent of epithelial regeneration was expressed as the percentage of the original wound area healed. After 4 days of treatment, monkeys were sacrificed by injection of T-61 euthanasia solution, and the corneas removed, fixed in 10% neutral buffered formalin, processed through paraffin, sectioned, and stained with hematoxylin and eosine.

4. Corneal Stromal Wounds

A full thickness central corneal incision 5 mm long was made in both eyes of anesthetized female Macaca fascicularis monkeys. Two drops of Neodecardron ® containing hEGF at the final concentration of 0.1 mg/ml were applied to the experimental eyes three time daily. Control eyes were similarly treated with Neodecardron ® alone. On days 6 and 9 the corneal lacerations were examined by slit lamp microscopy and photographed. After 9 days of treatment the extent of wound healing was measured by introducing a 25 gauge cannula into the anterior chamber at the corneal/scleral junction and the intraocular pressure was gradually raised using a Tycos handheld aneroid manometer. The pressure required to initiate leaking and then bursting of the wound was determined and results were analyzed using the student paired T-test. At the end of the experiment, monkeys were sacrificed by intravenous administration of T-61 euthanasia solution, and eyes were enucleated, fixed in 10% neutral buffered formalin, embedded in paraffin, sectioned, stained by hematoxylin and eosine, and then examined for histological evidence of wound healing.

5. Split Thickness Cutaneous Wounds

Four white Vita-Vet ® adult miniature pigs (50–60 lbs) were shaved in the thoracic and paravertebral areas. Each pig was anesthetized with ketamine. Seventy-five 10 mm×100 mm split thickness wounds were created on each pig with a modified Castro-Viejo dermatome. The wounds were 0.005 inches deep and were placed 1 cm apart. There were 3 groups of wounds on each pig. Group 1 received topical treatment of saline alone. Group 2 received topical lanolin cream (Squibb and Sons, Princeton, NJ). Group 3 received topical lanolin cream with 10 μg/ml of hEGF. Each wound received ⅓ ml of the appropriate treatment per wound every 12 hours. Twenty-four hours after the initial wounding, four wounds from each group on each pig were entirely excised using a standard blade (22 mm wide). The wound, as well as the surrounding non-wounded skin, was removed. The dermatome was set to a depth of 0.007 inches. The excised specimens were incubated overnight in a 1% trypsin broth at 4° C. The epidermis was easily separated from the dermis on the following day. When no defect was visible in the separated epidermis, the specimen was considered healed. Four wounds from each group were excised each day for 6 days.

The above experiment was repeated with the exception that Group 1 received treatment with Silvadene ® alone and Group 2 received treatment with Silvadene ® having hEGF at 10 μg/ml.

RESULTS

1. Corneal Epithelial Regeneration

Quantitative planimetry of the fluorescein stained region of the corneas indicated during the first two days after removal of the epithelium that hEGF-Neodecadron ® significantly ($p<0.05$, Chi square analysis) increased the percentage of corneal surface that has re-epithelialized. During the next two days of treatment (days 3 and 4) the eyes treated with Neodecadron ® containing hEGF all healed completely, as did 2 of the 4 control corneas treated with Neodecadron ® alone. The rates of healing in control corneas treated with Neodecadron ® alone were linear in all four control corneas until approximately 80 to 90 percent of the initial wound was healed; then the rate of healing decreased. In contrast, the hEGF-Neodecadron ®-treated corneas consistently displayed curvilinear healing rates with a rapid initial rate of healing which decreased as the wound neared complete healing.

Histological examination of the regenerated epithelium of Neodecadron ®-treated corneas revealed 3 to 5 cell layers with tall cuboidal basal cells with pale-staining cytoplasm, and large irregular nuclei characteristic of proliferating basal epithelial cells in middle to end stages of wound healing. In contrast, hEGF-Neodecadron ®-treated corneas had 4 to 6 cell layers with cuboidal, basal cells with dark-staining cytoplasm and homogeneous nuclei which are typical of a normal epithelium.

2. Corneal Stromal Wound Healing

After nine days of treatment, the pressure which caused leaking in the anterior chamber and then bursting of the corneal wounds was measured. Treatment with hEGF-Neodecardon ® significantly increased both the leaking and bursting pressures compared to corneas treated with Neodecadron ® along. Further, treatment with hEGF-Neodecadron ® increased wound strength relative to Neodecadron ® alone both when the epithelium was intact and when the epithelium was removed at the start of the experiment ($p<0.001$). Complete removal of the corneal epithelium before the laceration was made caused significantly less healing both in hEGF-treated corneas ($p<0.01$) and in the control corneas ($p<0.001$) compared to wounds made in corneas with intact epithelium. This suggests that the presence of epithelium aids the process of stromal wound healing.

Histological examination of the corneal wounds revealed that a plug of epithelial cells extended the full length of the cut in the Neodecadron ®-treated eye. In contrast, a plug of epithelial cells extended only about one-third of the length of the cut in the hEGF-Neodecadron ®-treated eye. In the remaining portion of the wound, the edges were no longer clearly discernible, but had merged and strands of fibrous material (presumably collagen) spanned the tract of the wound. Examination of the wounds by slit biomicroscopy indicated that the wounds in the hEGF-Neodecadron ®-treated eyes were narrow and appeared healed, while the wounds treated with Neodecadron ® alone appeared wide and unhealed.

3. Split Thickness Cutaneous Wound Healing

Fifty percent (8) of the wounds treated with hEGF-lanolin (N=16) were healed at day 2. The lanolin alone and saline-treated control groups required greater than 4 days before 50% of the excised wounds were healed ($p<0.001$). All wounds (N=16) excised on day 6 were healed. The results were as follows.

| | Percentage of Wounds Healed | | | | | |
|---|---|---|---|---|---|---|
| treatment | Day 1 | Day 2 | Day 3 | Day 4 | Day 5 | Day 6 |
| Saline controls | 0 | 0 | 17 | 33 | 83 | 100 |
| Lanolin alone | 0 | 0 | 0 | 40 | 80 | 100 |
| hEGF-Lanolin | 0 | 50 | 83 | 100 | 100 | 100 |

Treatment with hEGF-Silvadene ® resulted in 62% healing on the second day and 100% healing by the fifth day. In contrast, treatment with saline or Silvadene ® along resulted in no healing until the fourth day and complete healing only after seven days. The results were as follows.

| | Percentage of Wounds Healed | | | | | | |
|---|---|---|---|---|---|---|---|
| Treatment | Day 1 | Day 2 | Day 3 | Day 4 | Day 5 | Day 6 | Day 7 |
| Saline controls | 0 | 0 | 0 | 36 | 68 | 80 | 100 |
| Silvadene ® alone | 0 | 0 | 0 | 36 | 44 | 70 | 100 |
| hEGF-Silvadene ® | 0 | 62 | 70 | 75 | 100 | 100 | 100 |

4. Full-Thickness Cutaneous Wound Healing

Twenty male Sprague-Dawley rats weighing 350 g were included in this study. On the dorsum of each animal, a 3 cm interscapular skin incision through the panniculus carnosus was created in order to simulate a primary surgical wound. Ten of the animals were randomly assigned to group A, while the remaining ten animals were assigned to group B. Each animal of group A received 1 cc of "ointment A" and the animals of group B received a like amount of "ointment B". The ointment was applied in the base of the wound prior to closure of the wound with metal staples. The study was double-blinded, where "ointment A" consisted of 10 $\mu$g/ml of hEGF in K-Y jelly and "ointment B' consisted of K-Y jelly alone.

Each animal was housed separately, and ten days post-incision the animals were sacrificed in a $CO_2$ chamber. The wounds were entirely excised with the panniculus carnosus in a 3 cm$\times$3 cm rectangle. Those animals in group A had no evidence of the incision when viewed dermal-side up. The animals in group B, however, has a visible defect remaining where the incision was placed when viewed dermal-side up. Burst strength measurement and hydroxyproline assays were all higher in the animals in group A than those in group B. These data indicate that hEGF enhances collagen synthesis as well as epithelialization, and, therefore, is potentially applicable in the treatment of many different types of surgical incisions.

EXAMPLE 2

This example illustrates the advantages of using a sustained release formulation of hEGF in cutaneous wound healing.

Materials and Methods

1. Preparation and purification of hEGF polypeptide hEGF was prepared and purified as in Example 1.

2. Formulation of hEGF

Four formulations of hEGF were prepared.
(1) hEGF in phosphate buffered saline (PBS), 1:4 w/v;
(2) hEGF in 1% hyaluronic acid, 1:4 w/v;
(3) single lamellar liposomes containing hEGF; and
(4) multilamellar liposomes containing hEGF.

Multilamellar liposomes containing hEGF were prepared as follows. Briefly, lecithin (50 mg) was added to a 12$\times$75 glass test tube and the hexane vehicle was evaporated under a stream of nitrogen. one ml of PBS containing 1 mg of hEGF was added and immediately vortexed and sonicated, then the liposomes were separated from the solution by centrifugation at 20,000$\times$g for 20 min or by gel filtration through a 25 cm column of Agarose 4B. Single lamellar liposomes were prepared as follows. Briefly, a mixture of lipids containing lecithin, phosphatidylglycerol, and cholesterol were added to a round bottom flask, 5 ml of ether added and dried under a nitrogen stream. Five ml of ether was added followed by one ml of hEGF (1 mg/ml) in PBS then immediately sonicated. The organic phase was removed by rotary evaporation and the single lamellar liposomes were formed, then purified by gel filtration or centrifugation as above. The amount of hEGF entrapped in liposomes was calculated by measuring the amount of trace $^{125}$I-EGF present in the purified liposomes.

3. Wound Model (a) Sustained Release Formulation Tests

Adult male Sprague Dawley rats weighing 230-250 g were anesthetized and a single interscapular incision 5 cm long penetrating the panniculus carnosus was created in the dorsal midline. Equal amounts of hEGF (10 $\mu$g) formulated in one of the four formulations were placed in the base of individual incision tracts, and then sutured. At daily intervals, rats were sacrificed by carbon dioxide inhalation and incisions with 3 mm of surrounding nonwounded skin were excised to the underlying muscle. Total amounts of hEGF present in incision areas were calculated by measuring residual $^{125}$I-hEGF present in samples using a Beckman 4000 gamma scintillation counter, and were expressed as percentages of original hEGF applied to incisions. At each time point, the average amount of hEGF retained in the incision for each formulation was calculated from the values from three rats. From each incision, three test strips approximately 5 mm wide were cut perpendicular to the original incision, one from the middle and two from each end. Measurements of incision strength were conducted using a Unite-O-Matic FM-20 tensiometer instrument. For each formulation, the mean tensile strength was calculated from the mean value of all incision measurements in the group.

(b) Repeated Doses of hEGF

Interscapular incisions were created as above on the backs of 22 rats and a perforated catheter was placed in the base of the incision and brought out through a separate stab incision at the base of the neck. Incisions of half the rats were treated three times a day for five days by rapidly injecting 200 $\mu$l of PBS containing 50 $\mu$g of hEGF, while the control rats received injections of PBS. Seven and 14 days after surgery, rats were sacrificed by carbon dioxide asphixiation, incisions and surrounding tissue were removed as above. Three strips were taken from tensile strength measurement from each incision.

c. Results (1) Retention of hEGF in Incisions

Approximately 20% of the $^{125}$I-hEGF formulated in saline or 1% hyaluronic acid was retained in the incision 1 day after surgery, and about 10% was retained after 2 days. Slightly more $^{125}$I-hEGF was retained in incisions when formulated in single lamellar liposomes (about 30% after 1 day, dropping to less than 10% after 3 days). Very substantial levels of $^{125}$I-EGF were retained in incisions for extended periods by multilamellar liposomes entrapping EGF (approximately 60% after 1 day and 10% after 5 days).

(2) Effect of hEGF Administration on Tensile Strength.

The results of administering a single dose of hEGF in saline to incisions are reported in Table 1 below.

TABLE 1

Tensile Strength of Incisions Treated with EGF Saline

An interscapular incision was made on the back of rats, and before suturing, each received 1 ml of saline, 1 ml of saline containing 10 $\mu$g of EGF, or no treatment. After 10 days, rats were sacrificed and triplicate tensile strength tests were conducted for each incision. Values are the means and standard deviation and n is the number of tensile strength measurements.

| Treatment | Tensile Strength (kg/cm²) | n |
|---|---|---|
| untreated | 2.84 ± 0.68 | 28 |
| saline | 2.64 ± 0.69 | 20 |
| EGF-saline | 2.81 ± 0.96 | 20 |

As shown, the average tensile strength of incisions treated with hEGF was not significantly stronger after 10 days than incisions treated either with PBS or simply sutured.

The results of administering repeated doses of hEGF in saline to incisions is shown in Table 2.

Table 2

Tensile Strength of Incisions Treated with Repeated Doses of EGF-Saline

An interscapular incision was made on the back of each rat and a perforated catheter was placed in the base of the incision and brought out through a separate stab wound and the incision was sutured. Incisions were treated three times a day for five days by injecting 200 $\mu l$ of saline alone or containing 50 $\mu g$ EGF. After seven and fourteen days, rats were sacrificed and triplicate tensile strength measurements were determined for each rat. Values are mean and standard deviation and n is the number of tensile strength measurements.

| Treatment | Tensile Strength (kg/cm²) | |
|---|---|---|
| | 7 days | 14 days |
| hEGF-saline | 4.51 ± 1.54* (15) | 6.23 ± 1.34 (18) |
| saline | 3.33 ± 1.30 (18) | 6.55 ± 1.87 (15) |

*P = 0.0126

As shown, hEGF-treated incisions were an average of 35% stronger than saline treated incisions 7 days after surgery. Fourteen days after surgery, the tensile strength of EGF-treated and saline-treated incisions were not different. Microscopically, the tract of the hEGF-treated incision 7 days after surgery was very narrow with closely opposed edges. A plug of epidermal cells extended a short distance into the incision and then progressed into an intermittant string of cells. The most striking feature was a massive tube of fibroblast-like cells underlying the incision which presumably formed around the catheter. In comparison, the saline-treated incision was filled by a wide plug of epidermal cells extending the full length of the incision. A substantially smaller tube of fibroblast-like cells was present under the incision. The 14 day specimens were similar with narrow incision tracts and nearly absent tube structures.

The results of a single application of multilamellar liposomes containing hEGF on tensile strength of incisions is shown in Table 3.

TABLE 3

Tensile Strength of Incisions Treated with EGF-Liposomes

An interscapular incision was made on the back of rats, and before suturing, each received 1 ml of liposome suspension containing 5 $\mu g$ of EGF, an equal amount of blank liposomes, or saline. At weekly intervals rats were sacrificed and triplicate tensile strength measurements were determined for each rat. Values are the means and standard deviation and n is the number of measurements.

| Days | Untreated | Liposomes | EGF-Liposomes |
|---|---|---|---|
| | Experiment 1 | | |
| 7 | 0.66 = 0.12 (16) | — | 0.71 = 0.09 (15) |
| 10 | 1.97 = 0.36 (9) | — | 2.54 = 0.55 (9) |
| 14 | 1.36 = 0.35 (10) | 1.42 = 0.38 (10) | 4.04 = 1.13 (10) |
| 21 | 3.85 = 1.23 (9) | 3.67 = 1.19 (10) | 3.43 = 1.16 (9) |
| 28 | 10.21 = 2.75 (5) | 7.58 = 2.12 (9) | 8.30 = 0.87 (7) |
| | Experiment 2 | | |
| 7 | 1.95 = 0.55 (15) | 2.50 = 0.43 (18) | 6.45 = 4.45 (18) |
| 14 | 7.97 = 2.89 (15) | 6.64 = 4.13 (15) | 7.04 = 2.00 (18) |
| 21 | 13.38 = 7.17 (18) | 13.31 = 7.12 (18) | 19.89 = 3.85 (18) |
| 28 | 17.12 = 5.17 (18) | 24.06 = 10.68 (18) | 25.29 = 16.95 (18) |

The first experiment results shown in Table 3 indicate that early in the course of healing (14 days after surgery), incisions treated with hEGF-liposomes were significantly stronger (approximately 3 fold higher wound tear strengths) than incisions treated with blank liposomes or untreated incisions. Twenty one days after surgery, tensile strengths of control incisions had increased to equal the strength of hEGF-treated incisions. Twenty eight days after surgery, tensile strengths of all three treatment groups continued to increase and had similar tensile strengths.

Light and electron microscopy of incisions 14 days after treatment with hEGF-liposomes revealed a hypertrophic epidermal layer with deep, extensive rete-peg and hemidesmosome formation to an early basement membrane formed directly over the incision. Many active fibroblasts with marked rough endoplasmic reticulum were present in the incision accompanied by some new collagen formation. In comparison, untreated incisions or incisions treated with blank liposomes had substantially less hypertrophy of their epidermal layer with no rete-peg formation. At the ultrastructural level, both control incisions appeared to have less collagen repair and more tissue edema than the hEGF-treated incision.

Twenty-one day specimens all had normal epidermis with well defined basal lamina and all had begun remolding some of the damaged collagen with new mature, collagen which was typically found in small areas adjacent to active fibroblasts. The twenty-eight day specimen treated with hEGF had the ultrastructural appearance of a very strong scar with well formed, bonded, and complete collagen with sparce ground substance. Large numbers of very active fibroblasts were present in the incision tract. In contrast, fewer active fibroblasts were present in both control incisions and remodeling of collagen was less advanced with much more ground substance present giving the incisions an edematous appearance.

In the second experiment, tensile strengths were measured at 7, 14, 21 and 28 days after surgery. At 7 days, the average tensile strength for incisions treated with hEGF entrapped in multilamellar liposomes was approximately 3-fold higher than tensile strengths for blank liposomes of saline-hEGF incisions. At 14 days, tensile strengths of incisions treated with blank liposomes or saline-hEGF had reached the strength of incisions treated with multilamellar-hEGF liposomes. At 21 days, the strength of hEGF-liposome treated incisions was about 1.5-fold higher than incisions treated with saline-hEGF or blank liposomes, and at 28 days the strengths of all incisions had increased to approximately the same level.

In summary, the results of Example 2 show that it is advantageous to administer hEGF to cutaneous wounds via a regime that provides effective amounts of hEGF at the wound site over a prolonged time period (i.e., at least about three days).

EXAMPLE 3

This example illustrates a cream formulation of hEGF which provides diffusion controlled sustained release of hEGF. The hEGF was made in the manner described in Example 1.

A cream vehicle having the following composition was prepared:

| Independent | Wt % |
|---|---|
| Petrolatum | 10 |
| Mineral oil | 10 |
| Brij 72 | 1.5 |
| Brij 78 | 3.5 |
| Stearyl alcohol | 6.0 |
| Thixin R | 1.0 |
| Propylene glycol | 15 |
| Water | ~53 |
| Parabens (methyl & propyl) | 0.23 |

$^{125}$I-hEGF was mixed with a stock solution of unlabeled hEGF to an activity of 28 million cpm/ml. This mixture was blended with the cream vehicle to give a final hEGF concentration of 10 µg/ml and an activity of 1.5 million cpm per 0.2 g of cream. Known weights of the cream were spread on the membrane of a standard Frantz diffusion cell having a reservoir containing 7 ml of pBS, pH 7.4 Release of hEGF was monitored. The plot of percent release of hEGF vs. time $^{\frac{1}{2}}$ was linear.

EXAMPLE 4

This example illustrates sustained release formulations of hEGF comprising hEGF dispersed in a body of a semipermeable polymer. The hEGF was prepared as in Example 1.

hEGF was dilated in sterile PBS to concentrations of 500, 100, 20, 4 and 0.8 µg/ml and lyophilized. Ethylene-vinyl acetate (EVA) copolymer beads were mixed with methylene chloride to produce a 10% w/v casting solution. Approximately 0.1 ml of casting solution was added to the lyophilized hEGF and mixed. Pellets containing 25, 6.2, 1.1, 0.18 and 0.04 µg hEGF per pellet were made by drying the mixtures.

The pellets were implanted into intrasomal corneal pockets located 1.5 mm from the limbus in the eyes of pigmented adult rabbits. The rabbit corneas were observed for angiogenic response and graded as follows: 4+, profuse capillary growth; 3+, extensive capillary growth; 2+, moderate capillary growth; 1+, very little capillary growth; 0, no capillary growth. The results are tabulated below.

| hEGF Sample (mg/pellet) | Angiogenic Response |
|---|---|
| 25 | 4+ |
| 6.2 | 3+ |
| 1.1 | 2+ |
| 0.18 | 1+ |
| 0.04 | 1+ |
| 0 (control) | 0 |

Angiogenesis, the induction of new growth of new capillary endothelium from nearby existing blood vessels, occurs during wound healing. The results described above show that sustained release of hEGF from EVA pellets induced angiogenesis in this rabbit cornea assay.

According to the present invention, a wound treatment composition is provided which promotes the rapid healing of epithelial wounds, including both cutaneous wounds and corneal wounds. The compositions include a polypeptide product having an amino acid sequence based on the sequence of natural human epidermal growth factor in an amount effective to promote such healing. The compositions are found to enhance the regeneration of both the epithelial layer and underlying stromal layer resulting from deep wounds to the cornea.

Plasmid pYαEGF-23 was deposited at the American Type Culture Collection on 12 Aug. 1983 and granted accession no. 40079.

Although the foregoing invention has been described in some detail by way of illustration and examples for purposes of clarity of understanding, it will be obvious that certain changes and modifications may be practiced within the scope of the appended claims.

We claim:

1. A method for treating corneal stromal wounds to promote healing, said method comprising applying human epidermal growth factor (hEGF) to the wound, where said hEGF is produced by expressing an hEGF gene encoding a polypeptide having at least substantially the same amino acid sequence and the same corneal stromal wound-healing activity as naturally occurring human epidermal growth factor in a microorganism.

2. A method as in claim 1, wherein the hEGF is produced in yeast.

3. A method as in claim 2, wherein the yeast is transformed with a DNA construct carrying a hEGF gene under the transcriptional and translational control of regulatory sequences including secretory leader and processing signal sequences functional in yeast.

4. A method as in claim 1, wherein the hEGF is present in a physiologically acceptable carrier at from 1 µg/ml to 10 µg/ml.

5. A method as in claim 1 wherein the hEGF is applied continually to the wound over an extended time period.

6. A method as in claim 5 wherein the continual application is achieved via a sustained release dosage form.

7. A method as in claim 6 wherein the sustained release dosage form is liposomes.

8. A method as in claim 7 wherein the liposomes are multilamellar liposomes.

9. A method as in claim 5 wherein the sustained release dosage form comprises the hEGF incorporated into a semipermeable polymer.

10. A method as in claim 9 wherein the semipermeable polymer is ethylene-vinyl acetate copolymer.

11. A method as in claim 5 wherein the continual application is achieved via a multiplicity of intermittent doses.

12. A method for treating corneal stromal wounds to promote healing, said method comprising applying to the wound a polypeptide capable of stimulating the proliferation of epithelial and stromal cells, where said polypeptide is produced by growing, in a culture medium suitable for growth of yeast, a yeast host which has been transformed by an extrachromosomal element carrying a gene encoding a polypeptide having at least substantially the same amino acid sequence and the same corneal stromal wound-healing activity as naturally occurring human epidermal growth factor under the transcriptional and translational control of regulatory sequences including secretory leader and processing signal sequences functional in said yeast host.

13. A method as in claim 12, wherein the hEGF gene is composed of preferred yeast codons.

14. A method as in claim 12, wherein the polypeptide is present in a physiologically acceptable carrier at from 1 µg/ml to 10 µg/ml.

15. A method as in claim 12 wherein the hEGF is applied continually to the wound over an extended time period.

16. A method as in claim 15 wherein the continual application is achieved via a sustained release dosage form.

17. A method as in claim 16 wherein the sustained release dosage form is liposomes.

18. A method as in claim 18 wherein the liposomes are multilamellar liposomes.

19. A method as in claim 16 wherein the sustained release dosage form comprises the hEGF incorporated into a semipermeable polymer.

20. A method as in claim 20 wherein the semipermeable polymer is ethylene-vinyl acetate copolymer.

21. A method as in claim 15 wherein the continual application is achieved via a multiplicity of intermittent doses.

* * * * *